United States Patent [19]

Someya et al.

[11] Patent Number: 4,741,756
[45] Date of Patent: May 3, 1988

[54] PROPIONIC ACID THIOL ESTER DERIVATIVES AND HERBICIDAL COMPOSITIONS CONTAINING THEM

[75] Inventors: Shinzo Someya, Tokorozawa; Seigo Koura, Tokyo; Mikio Ito, Tokuyama; Akira Nakanishi, Yokohama; Yuji Nonaka, Tokuyama, all of Japan

[73] Assignees: Toyo Soda Mfg. Co., Yamaguchi; Agro-Kenesho Co., Ltd., Tokyo, both of Japan

[21] Appl. No.: 48,956

[22] Filed: May 12, 1987

[30] Foreign Application Priority Data

May 16, 1986 [JP] Japan .................. 61-11929

[51] Int. Cl.$^4$ .................. A01N 43/28; A01N 43/40; C07D 277/70; C07D 401/12
[52] U.S. Cl. .................. 71/90; 548/170; 548/187; 546/270; 546/280; 71/94
[58] Field of Search .................. 548/170, 187; 71/90

[56] References Cited

U.S. PATENT DOCUMENTS

| | | | |
|---|---|---|---|
| 3,954,442 | 5/1976 | Becker et al. | 548/170 |
| 4,130,413 | 12/1978 | Handte et al. | 548/170 |
| 4,238,626 | 12/1980 | Nahm et al. | 548/170 |
| 4,389,525 | 6/1983 | Bock | 548/187 |
| 4,391,995 | 7/1983 | Nahm et al. | 548/170 |
| 4,404,020 | 9/1983 | Schurter et al. | 548/170 |

FOREIGN PATENT DOCUMENTS

| | | | |
|---|---|---|---|
| 0000483 | 6/1978 | European Pat. Off. | 548/570 |
| 0003584 | 8/1979 | European Pat. Off. | 548/170 |
| 0115823 | 1/1984 | European Pat. Off. | 548/170 |
| 0111929 | 5/1986 | Japan | 548/170 |
| 2015995 | 3/1979 | United Kingdom | 548/170 |
| 1599121 | 7/1981 | United Kingdom | 548/170 |

*Primary Examiner*—Henry R. Jiles
*Assistant Examiner*—J. Richter
*Attorney, Agent, or Firm*—Nixon & Vanderhye

[57] ABSTRACT

A propionic acid thiol ester derivative having the formula:

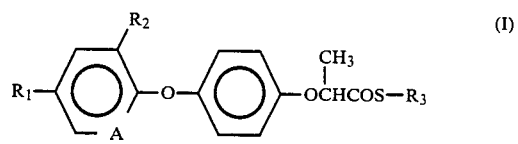

wherein $R_1$ is a cyano group, a trifluoromethyl group, a halogen atom or a nitro group, $R_2$ is a hydrogen atom, a halogen atom or a cyano group, $R_3$ is a thiazolin-2-yl group or a benzothiazol-2-yl group, and A is a methine group or a nitrogen atom.

7 Claims, No Drawings

PROPIONIC ACID THIOL ESTER DERIVATIVES AND HERBICIDAL COMPOSITIONS CONTAINING THEM

The present invention relates to novel phenoxy propionic acid thiol ester derivatives, processes for their production and selective herbicides containing them as active ingredients.

A number of phenoxy propionic acid ester derivatives have been reported for their herbicidal activities. For example, methyl 2-[4-trifluromethylphenoxy)-phenoxy]propionate, methyl 2-[4-(3,5-dichloro-2-pyridyloxy)phenoxy]propionate and butyl 2-[4-(5-trifluoromethyl-2-pyridyloxy)phenoxy]propionate have been known and practically used for controlling weeds. However, the herbicidal activities of these substances are not necessarily adequate for the following reasons.

For the cultivation of broad leaf crop plants such as sugar beet (*Beta vulgaris*), soybean (*Glycine max*), cotton (*Gossypium*), alfalfa (*Medicago sativa*), rape (*Brassica napus*), potato (*Solanum tuberosum*), sunflower (*Helianthus annuus*), radish (*Raphanum raphanistrum*), chinese cabbage, cabbage, and tomato, there is a strong demand in the market for a selective herbicide capable of killing gramineous weeds by either pre-emergence soil treatment or post-emergence foliage treatment without adversely affecting such crop plants, in spite of the fact that a number of herbicides have already been developed and marketed. Farmers for the crop plants have complained that when used for foliage treatment after the emergence of weeds, the above-mentioned conventional phenoxy propionic acid esters require at least 8 days before they become effective after the treatment, and their improvements in this respect have been strongly desired.

It is an object of the present invention to provide an improved selective herbicide which can industrially be produced and which satisfies the demand in the market.

The present invention provides a novel phenoxy propionic acid thiol ester derivative having the formula:

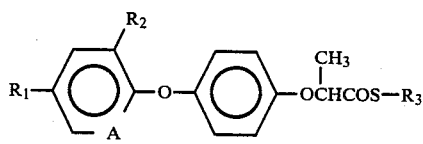

(I)

wherein $R_1$ is a cyano group, a trifluoromethyl group, a halogen atom or a nitro group, $R_2$ is a hydrogen atom, a halogen atom or a cyano group, $R_3$ is a thiazolin-2-yl group or a benzothiazol-2-yl group, and A is a methine group or a nitrogen atom (hereinafter referred to as the compound of the present invention).

The compound of the formula I of the present invention can be prepared by a process which comprises reacting a propionic acid halide of the formula:

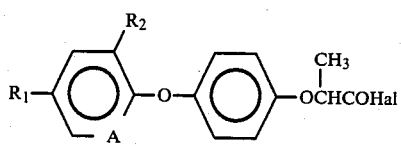

(II)

wherein $R_1$, $R_2$ and A are as defined above, and Hal is a halogen atom, with a mercaptan derivative of the formula:

$$HS-R_3 \quad (III)$$

wherein $R_3$ is as defined above, or a process which comprises reacting a phenol derivative of the formula:

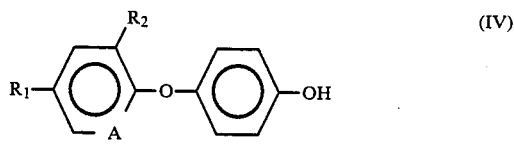

(IV)

wherein $R_1$, $R_2$ and A are as defined above, with a propionic acid thiol ester derivative of the formula:

(V)

wherein $R_3$ is as defined above, and Hal is a halogen atom.

The present invention also provides a herbicidal composition comprising a herbicidally effective amount of the compound of the formula I and an agricultural adjuvant.

Further, the present invention provides a method for killing weeds which comprises applying a herbicidally effective amount of the compound of the formula I to a locus to be protected.

The compound of the formula I has a feature that it shows a remarkably selective herbicidal activity.

Now, the present invention will be described in detail with reference to the preferred embodiments.

The compound of the present invention may be prepared by various methods. However, the representative processes are as shown below.

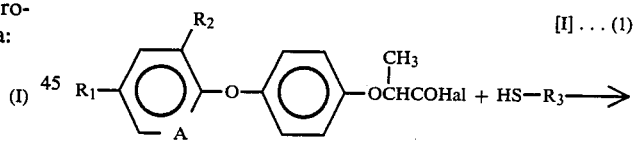

[I] ... (1)

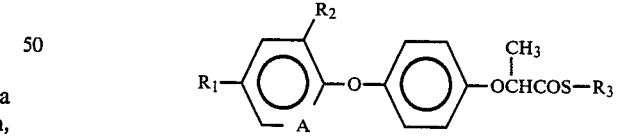

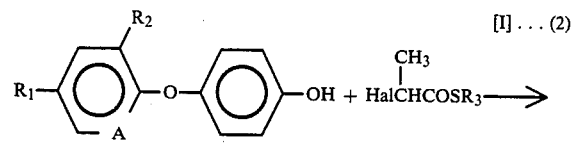

[I] ... (2)

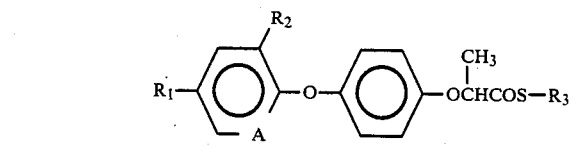

In the above formulas, $R_1$, $R_2$, $R_3$, A and Hal are as defined above.

These reactions can be conducted in the presence or absence of a solvent by using a suitable base to obtain the compound of the present invention. As the solvent, a ketone such as acetone or methyl ethyl ketone, an aromatic hydrocarbon such as benzene, toluene or xylene, an ether such as ethyl ether, tetrahydrofuran or dioxane, a halogenated hydrocarbon such as chlorobenzene, chloroform, carbon tetrachloride or dichloroethane, a tertiary amine such as triethylamine, pyridine or dimethylaniline, or a polar solvent such as dimethylformamide, dimethylsulfoxide or phosphoric acid hexamethyl triamide, may be employed.

As the base, a tertiary amine such as triethylamine, pyridine, 1,8-diazabicyclo-(5,4,0)-7-undecene or dimethylaniline, an alkali metal hydroxide such as sodium hydroxide or potassium hydroxide, an alkaline earth metal hydroxide such as calcium hydrxide, an alkali metal carbonate such as sodium carbonate, potassium carbonate, sodium hydrogencarbonate or potassium hydrogencarbonate, or a metal hydride such as sodium hydride, may be used. The reactions proceed usually at a temperature of from about 0° to about 150° C., preferably from about 20° to about 100° C. The reaction time is usually from a few minutes to about 48 hours.

When the compound of the present invention is to be used as a herbicide, it may be formulated into various formulations such as an emulsifiable concentrate, a wettable powder, a water soluble powder, an oil solution, a dust or granules, by using agricultural adjuvants in accordance with methods commonly employed for the preparation of agricultural formulations. Such various formulations may be used as they are or may be diluted with water to a predetermined concentration for practical application.

Specific examples of agricultural adjuvants include, for example, a diluent, a surfactant, a stabilizer, a binder, an aerosol propellant, and a synergistic agent. As the diluent, a solvent such as water, an organic solvent, a hydrocarbon, a halogenated hydrocarbon, an alcohol, an ether, an alcohol ether, a ketone, an ester, an amide or a sulfoxide, may be mentioned. As a filler or solid carrier, an inorganic powder such as slaked lime, magnesium lime, gypsum, calcium carbonate, silica, pearlite, pumice, diatomaceous earth, alumina, zeolite or clay minerals (such as talc, vermiculite or kaolinite), a vegetable powder (such as starch powder, cereals powder or glucose powder), or a synthetic resin powder (such as a phenol resin, a urea resin or a vinyl chloride resin), may be mentioend.

As the surfactant, an anionic surfactant (such as an alkyl sulfate, an aryl sulfonic acid, a succinate or a polyethylene glycol alkylaryl ether sulfate), a cationic surfactant (such as an alkylamine or a polyoxyethylene alkylamine), a nonionic surfactant (such as a polyoxyethylene glycol ether, a polyoxyethylene glycol ester or a polyhydric alcohol ester), or an amphoteric surfactant may be mentioned.

As other adjuvants, a stabilizer, a binder, an effect-prolonging agent, a dispersant and a synergistic agent may be mentioned.

In the herbicidal composition of the present invention, the compound of the formula I is incorporated as an active ingredient usually in an amount of from 0.1 to 90% by weight, preferably from 1 to 80% by weight.

In the actual application, the dose of the compound of the present invention as the active ingredient may suitably be adjusted depending upon the type of the formulation, the manner, object or season for the application, or the state of the germination of weeds. The dose is usually within a range of from 0.05 to 10 kg/ha, preferably from 0.1 to 5 kg/ha.

Now, the present invention will be described in further detail with reference to Preparation Examples, Formulation Examples and Test Examples. However, it should be understood that the present invention is by no means restricted to these specific Examples.

EXAMPLE 1

2-[4-(4-cyanophonexy)phenoxy]propionic acid 2'-benzothiazole thioester (Compound No. 1)

1.16 g of 2-mercapto benzothiazole was dissolved in 30 ml of tetrahydrofuran/dichloromethane=1/5 (v/v). Then, a solution of 2.1 g of 2-[4-(4-cyanophenoxy)-phenoxy]propionic acid chloride in 10 ml of dichloromethane was dropwise added thereto at room temperature. The mixture was stirred for 10 minutes, and 0.7 g of triethylamine was added. The mixture was stirred for 8 hours at room temperature. Then, water was added to the reaction mixture, and the dichloromethane solution was separated, washed with water and dried over anhydrous magnesium sulfate. Then, the solvent was distilled off, and the residue was purified by column chromatography [silica gel, benzene/ethyl acetate=10/1 (v/v)] to obtain 1.43 g of the desired product having a melting point of from 178° to 181° C.

EXAMPLE 2

2-[4-(4-trifluoromethylphenoxy)phenoxy]propionic acid 2'-benzothiazole thioester (Compound No. 7)

0.51 g of 2-mercapto benzothiazole was dissolved in 30 ml of tetrahydrofuran/dichloromethane=1/5 (v/v). Then, a solution of 106 g of 2-[4-(4-cyanophenoxy)-phenoxy]propionic acid chloride in 10 ml of dichloromethane was dropwise added thereto at room temperature. The mixture was stirred for 10 minutes, and 0.13 g of triethylamine was added thereto. The mixture was stirred for 8 hours at room temperature. Then, water was added to the reaction mixture, and the dichloromethane solution was separated, washed with water and dried over anhydrous magnesium sulfate. Then, the solvent was distilled off, and the residue was purified by column chromatography [silica gel, benzene/ethyl acetate=10/1 (v/v)] to obtain 0.5 g of the desired product having a melting point of from 169° to 173° C.

Representative examples of the compound of the present invention will be given in Table 1.

TABLE 1

$R_1-C_6H_3(R_2)(A)-O-C_6H_4-OCH(CH_3)COS-R_3$

| Compound No. | $R_1$ | $R_2$ | A | $R_3$ | Physical property |
|---|---|---|---|---|---|
| 1 | NC | H | CH | 2-benzothiazolyl | mp 178–181° C. |

TABLE 1-continued

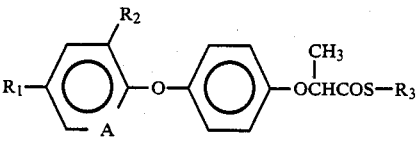

| Compound No. | R₁ | R₂ | A | R₃ | Physical property |
|---|---|---|---|---|---|
| 2 | NC | H | CH | 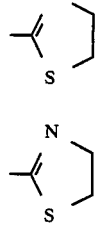 | $n_D^{25}$ 1.6374 |
| 3 | F₃C | H | N | 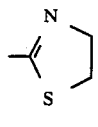 | mp 105–106° C. |
| 4 | NC | H | N | 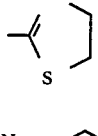 | mp 126–128° C. |
| 5 | Cl | Cl | N |  | mp 111–114° C. |
| 6 | Cl | Cl | CH |  | mp 173–176° C. |
| 7 | F₃C | H | CH |  | mp 169–173° C. |
| 8 | O₂N | H | CH |  | mp 130–135° C. |
| 9 | Br | CN | CH |  | $n_D^{25}$ 1.6300 |
| 10 | F₃C | Cl | CH |  | mp 130–134° C. |
| 11 | NC | Cl | CH |  | mp 176–179° C. |
| 12 | F₃C | Cl | N |  | $n_D^{25}$ 1.5939 |

EXAMPLE 3

Emulsifiable concentrate

20 Parts ("parts" means "parts by weight", and the same applies hereinafter) of Compound No. 2 of the present invention, 60 parts of xylene, 20 parts by Sorpol 2806B (tradename, manufactured by Toho Kagaku Kogyo K.K.) were uniformly mixed and stirred to obtain an emulsifiable concentrate.

EXAMPLE 4

Wettable powder

10 Parts of white carbon, 65 parts of jeeklite, 5 parts of Sorpol 5039 (tradename, manufactured by Toho Kagaku Kogyo K.K.) and 20 parts of Compound No. 3 of the present invention were mixed and pulverized to obtain a wettable powder.

EXAMPLE 5

Soil treatment test

Soil was put into a 1/5000 are Wagner pot, and cultivated to simulate a field. Then, prescribed amounts of seeds of barnyardgrass (*Echinochloa crus-galli*), radish and soybean were sown, and covered with soil containing seeds of gramineous weeds such as large crabgrass (*Digitaria sanguinalis*), barnyardgrass (*Echinochloa crus-galli.* Beauv.) and green foxtail (*Setaria viridis*) in a thickness of about 1 cm. On the 3rd day after seeding, a herbicide solution having a predetermined concentration was uniformly sprayed. On the 22nd day, the states of the weeds and crop plants were examined, and the results are shown in Table 2. The growth controlling degree was rated by five numerical values of from 1 to 5 (1: No effect at all, 5: Complete kill).

TABLE 2

| Compound No. | Dose of active ingredient (kg/ha) | Growth controlling degree | | | |
|---|---|---|---|---|---|
| | | Rap | Gly | Ech | Gramineous weeds |
| 2 | 1 | 1 | 1 | 5 | 5 |
| | 0.5 | 1 | 1 | 5 | 5 |
| 7 | 1 | 1 | 1 | 5 | 5 |
| | 0.5 | 1 | 1 | 5 | 5 |
| 10 | 1 | 1 | 1 | 5 | 5 |
| | 0.5 | 1 | 1 | 4 | 4–5 |
| 11 | 1 | 1 | 1 | 5 | 5 |
| | 0.5 | 1 | 1 | 4–5 | 5 |
| 12 | 1 | 1 | 1 | 5 | 5 |
| | 0.5 | 1 | 1 | 5 | 5 |
| Comparative Compound (A) | 1 | 1 | 1 | 5 | 5 |
| | 0.5 | 1 | 1 | 5 | 4 |
| Comparative Compound (B) | 1 | 1 | 1 | 5 | 5 |
| | 0.5 | 1 | 1 | 5 | 4 |
| Comparative Compound (C) | 1 | 1 | 1 | 5 | 5 |
| | 0.5 | 1 | 1 | 4 | 3 |
| Non-treated area | — | 1 | 1 | 1 | 1 |

Rap: radish (*Raphanus raphanistrum*)
Gly: soybean (*Glycine max*)
Ech: barnyardgrass (*Echinochloa crus-galli*)

COMPARATIVE COMPOUND (A): Ethyl 2-[4-(4-trifluoromethylphenoxy)phenoxy]propionate
COMPARATIVE COMPOUND (B): Butyl 2-[4-(5-trifluoromethyl-2-pyridyloxy)phenoxy]propionate
COMPARATIVE COMPOUND (C): Methyl 2-[4-(2,4-dichlorophenoxy)-phenoxy]propionate

EXAMPLE 6

Cultivation was conducted in the same manner as in Example 5, and when the weeds reached 3–3.5 leaf stage, a herbicide having a predetermined concentration was uniformly applied to the foliage. The states of growth of the weeds were examined on the 5th day and the 10th day after the treatment, and the results are shown in Tables 3 and 4. The numerical values for the growth controlling degree are the same as in Example 5.

TABLE 3

| Compound No. | Concentration of active ingredient (ppm) | Effect on the 10th day after the foliage treatment | | | | | |
|---|---|---|---|---|---|---|---|
| | | Ech | Ave | Set | Dig | Pha | Rap |
| 1 | 2,000 | 3 | — | — | — | — | — |
| 2 | " | 5 | 5 | 5 | 5 | 1 | 1 |
| 3 | " | 5 | 5 | 5 | 5 | 1 | 1 |
| 4 | " | 5 | 3 | 3 | 3 | 1 | 1 |
| 5 | " | 5 | 4 | 5 | 4 | 1 | 1 |
| 6 | " | 5 | 3 | 4 | 5 | 1 | 1 |
| 7 | " | 5 | 5 | 5 | 5 | 1 | 1 |
| 8 | " | 4 | 3 | 4 | 3 | 1 | 1 |
| 9 | " | 5 | 4 | 4 | 4 | 1 | 1 |
| 10 | " | 5 | 5 | 5 | 5 | 1 | 1 |
| 11 | " | 5 | 5 | 5 | 5 | 1 | 1 |
| 12 | " | 5 | 5 | 5 | 5 | 1 | 1 |
| Non-treated area | — | 1 | 1 | 1 | 1 | 1 | 1 |

Ech: barnyardgrass (*Echinochloa crus-galli*)
Ave: oat (*Avena sativa*)
Set: green foxtail (*Setaria viridis*)
Dig: large crabgrass (*Digitaria sanguinalis*)
Pha: mung bean (*Phaseolus mungo* L.)
Rap: radish (*Raphanus raphanistrum*)

TABLE 4

| Compound No. | Concentration of active ingredient (ppm) | on the 5th day after the treatment | | | | On the 10th day after the treatment | | | |
|---|---|---|---|---|---|---|---|---|---|
| | | Ech | Ave | Set | Dig | Ech | Ave | Set | Dig |
| 2 | 500 | 5 | 5 | 5 | 5 | — | — | — | — |
| | 250 | 5 | 5 | 5 | 5 | — | — | — | — |
| 7 | 500 | 5 | 5 | 5 | 5 | — | — | — | — |
| | 250 | 5 | 5 | 5 | 5 | — | — | — | — |
| 10 | 500 | 5 | 5 | 5 | 5 | — | — | — | — |
| | 250 | 4 | 3 | 3 | 4 | — | — | — | — |
| 11 | 500 | 5 | 5 | 5 | 5 | — | — | — | — |
| | 250 | 4 | 2 | 4 | 3 | — | — | — | — |
| 12 | 500 | 5 | 5 | 5 | 5 | — | — | — | — |
| | 250 | 5 | 5 | 5 | 5 | — | — | — | — |
| Comparative Compound (A) | 500 | 1 | 1 | 1 | 1 | 5 | 5 | 5 | 5 |
| | 250 | 1 | 1 | 1 | 1 | 5 | 4 | 5 | 5 |
| Comparative Compound (B) | 500 | 1 | 1 | 1 | 1 | 5 | 4 | 5 | 5 |
| | 250 | 1 | 1 | 1 | 1 | 5 | 3 | 5 | 5 |
| Comparative Compound (3) | 500 | 1 | 1 | 1 | 1 | 5 | 3 | 5 | 5 |
| | 250 | 1 | 1 | 1 | 1 | 4 | 1 | 3 | 4 |
| Non-treated area | — | 1 | 1 | 1 | 1 | 1 | 1 | 1 | 1 |

Ech: barnyardgrass (*Echinochloa crus-galli*)
Ave: oat (*Avena sativa*)
Set: green foxtail (Setaria viridis)
Dig: large crabgrass (*Digitaria sanguinalis*)

Comparative Compounds (A), (B) and (C) are the same as the Comparative Compound used in Example 5.

The compounds of the present invention have excellent selectivity for crop plants such as beans, cotton (*Gossypium indicum*), carrot, potato (*Solanum tuberosum*), sugar beet (*Beta vulgaris*), cabbage (*Brassica oleracea* linnaeus var. *capitata*), indian mustard (*Brassica juncea*), wild mustard (*Brassica kaber* var. *pinnatifida*), peanut (*Arachis hypogaea*), radish (*Raphanus raphanistrum*), tobacco, tomato and cucumber (*Cucumis sativus*), i.e. they do not bring about any phytotoxicity at a concentration usually employed. Thus, they exhibit superior selective herbicidal activities against weeds, particularly against gramineous weeds such as barnyardgrass (*Echinochloa oryzicola*), large crabgrass (*Digitaria sanguinalis*), goosegrass (*Eleusine indica*), green foxtail (*Setaria viridis*), wild oat, water foxtail (*Alopecurus aequalis*), yellow foxtail (*Setaria glauca*), quackgrass (*Agropyron repens*), *Agropyron tsukushiense* var. *transiens*, bermudagrass (*Cynodon dactylon*) and johnsongrass (*Sorghum halepense*), by pre-emergence soil treatment or by post-emergence foliage treatment.

Further, as shown by the Examples, the compound of the present invention has a feature that when used for the post-emergence foliage treatment of weeds, the herbicidal activities appear within 4 to 5 days, i.e. substantially facilitated as compared with the conventional similar compounds.

We claim:
1. A propionic acid thiol ester derivative having the formula:

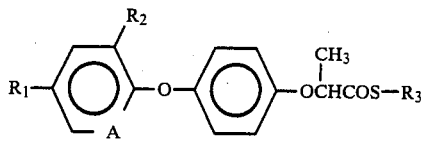

(I)

wherein $R_1$ is a cyano group, a trifluoromethyl group, a halogen atom or a nitro group, $R_2$ is a hydrogen atom, a halogen atom or a cyano group, $R_3$ is a thiazolin-2-yl group or a benzothiazol-2-yl group, and A is a methine group.

2. The compound of the formula I according to claim 1, wherein $R_1$ is a cyano group, $R_2$ is a hydrogen atom, $R_3$ is a thiazolin-2-yl group, and A is a methine group.

3. The compound of the formula I according to claim 1, wherein $R_1$ is a trifluoromethyl group, $R_2$ is a hydrogen atom, $R_3$ is a benzothiazol-2-yl group, and A is a methine group.

4. The compound of the formula I according to claim 1, wherein $R_1$ is a trifluoromethyl group, $R_2$ is a chlorine atom, $R_3$ is a benzothiazol-2-yl group, and A is a methine group.

5. The compound of the formula I according to claim 1, wherein $R_1$ is a cyano group, $R_2$ is a chlorine atom, $R_3$ is a benzothiazol-2-yl group, and A is a methine group.

6. A herbicidal composition comprising a herbicidally effective amount of a propionic acid thiol ester derivative of the formula I as defined in claim 1 and an agricultural adjuvant.

7. A method for killing weeds which comprises applying a herbicidally effective amount of a propionic acid thiol ester derivatiye of the formula I as defined in claim 1 to a locus to be protected.

* * * * *